US009414850B2

(12) United States Patent
Cleveland et al.

(10) Patent No.: US 9,414,850 B2
(45) Date of Patent: Aug. 16, 2016

(54) METHODS AND DEVICES FOR REMOVING ABNORMALITIES FROM BONE

(71) Applicant: DePuy Mitek, LLC, Raynham, MA (US)

(72) Inventors: Benjamin Cleveland, North Grafton, MA (US); Marc Helmick, Brighton, MA (US); John R. Cournoyer, Norfolk, MA (US); Michael Defusco, North Attleboro, MA (US); Donald Barry, Norwood, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 14/727,015

(22) Filed: Jun. 1, 2015

(65) Prior Publication Data

US 2015/0257771 A1    Sep. 17, 2015

Related U.S. Application Data

(62) Division of application No. 13/755,937, filed on Jan. 31, 2013, now Pat. No. 9,084,615.

(51) Int. Cl.
*A61B 17/00* (2006.01)
*A61B 17/16* (2006.01)

(52) U.S. Cl.
CPC .......... *A61B 17/1659* (2013.01); *A61B 17/1617* (2013.01); *A61B 17/1668* (2013.01)

(58) Field of Classification Search
CPC ........... A61B 17/1668; A61B 17/1659; A61B 17/1617; A61B 17/1671; A61B 17/1604
USPC .......... 606/79, 83, 84, 170, 182, 183; 30/152, 30/153, 172, 173, 182, 87, 299, 304
See application file for complete search history.

(56) References Cited

U.S. PATENT DOCUMENTS

| 2,077,804 | A | 4/1937 | Stearns et al. |
| 5,245,987 | A | 9/1993 | Redmond et al. |
| 9,084,615 | B2 | 7/2015 | Cleveland et al. |
| 2005/0113836 | A1 | 5/2005 | Lozier et al. |
| 2006/0052670 | A1 | 3/2006 | Stearns et al. |
| 2007/0016211 | A1 | 1/2007 | Botimer |
| 2007/0060933 | A1* | 3/2007 | Sankaran ............ A61B 17/16 606/160 |
| 2008/0009877 | A1 | 1/2008 | Sankaran et al. |
| 2009/0306586 | A1 | 12/2009 | Ross et al. |
| 2011/0152868 | A1* | 6/2011 | Kourtis ............... A61B 17/025 606/80 |
| 2012/0330318 | A1* | 12/2012 | Gerges ............... A61B 17/175 606/89 |

* cited by examiner

*Primary Examiner* — Christopher Beccia
*Assistant Examiner* — Diana S Jones

(57) ABSTRACT

Various exemplary methods and devices are provided for removing abnormalities from bone. In general, the methods and devices can be used to allow excess bone to be scraped from a bone surface. In an exemplary embodiment, a scraper tool is provided that includes an elongate shaft having a plurality of blades movably disposed therein. The blades can be configured to move as a unit between a retracted configuration, in which the blades can be entirely disposed within the elongate shaft, and an advanced configuration, in which at least a portion of the blades can extend distally from the elongate shaft and/or flare away from one another. A distal portion of each of the blades can have a radius of curvature corresponding to a radius of curvature of the bone to be scraped.

8 Claims, 4 Drawing Sheets

METHODS AND DEVICES FOR REMOVING ABNORMALITIES FROM BONE

CROSS-REFERENCE TO RELATED APPLICATIONS

This application is a divisional of U.S. application Ser. No. 13/755,937 filed on Jan. 31, 2013, and entitled "Methods and Devices for Removing Abnormalities from Bone," which is hereby incorporated by reference herein in its entirety.

FIELD

The present disclosure relates generally to methods and devices for removing abnormalities from bone.

BACKGROUND

Bone abnormalities are a relatively commonplace pathology that can require surgical intervention. For example, a CAM lesion L, shown in FIG. 1, is a type of excess bone growth that occurs on a femoral neck N of a femur F. The CAM lesion L reduces a range of motion of a head H of the femur F within an acetabulum A of a pelvis P, as shown in FIGS. 2 and 3. A normal range of motion of a normal femur F2 is shown in FIGS. 4 and 5. The femeroacetabular impingement caused by the CAM lesion L can have serious consequences, such as soft tissue damage, pain, and inhibited lifestyle.

Surgical procedures for removing bone abnormalities such as CAM lesions are traditionally performed arthroscopically using a rotating burr to remove excess bone. The surgery is performed by waving the burr over the surface of the bone. To ensure that the burr does not deviate from a desired path, the surgeon must have a complete understanding of the geometry of the bone abnormality and of the curvature of the bone from which it is removed. Given the complex, curved geometry of the femoral neck and the variability among bone abnormalities, the requisite knowledge can be difficult to acquire prior to surgery and there can be an increased risk of accidental removal of normal bone and/or damage to surrounding soft tissue. The surgeon must therefore proceed slowly over a localized region of the bone, which can reduce the effectiveness and/or the efficiency of the procedure, and in some cases may still not effectively prevent the burr from removing normal bone and/or damaging soft tissue.

To lower risks associated with using a burr to remove bone, the surgeon traditionally must be able to view the bone being reshaped during surgery, e.g., by a camera, to ensure that only abnormal bone is removed. However, the camera must be repeatedly moved throughout the surgery to different positions in order to view the area being reshaped. This constant repositioning during the surgery can create inefficiency and/or can increase the risk of soft tissue damage by the camera and/or the surgical tools used to reposition the camera.

Accordingly, there remains a need for improved methods and devices for removing abnormalities from bone.

SUMMARY

The present invention generally provides methods and devices for removing abnormalities from bone. In one aspect, a surgical device is provided that includes an elongate shaft having an inner passageway extending therethrough in at least a distal portion thereof. The elongate shaft can be configured to be advanced into a body of a patient. The surgical device can also include a plurality of blades, each having a curved distal end configured to contact a bone of the patient. The plurality of blades can be selectively moveable as a unit between a retracted configuration in which the plurality of blades are disposed within the inner passageway and an advanced configuration in which the plurality of blades are advanced out of the inner passageway such that the curved distal ends are outside the inner passageway. The plurality of blades can be configured to move away from one another when the plurality of blades move from the retracted configuration to the advanced configuration, and the plurality of blades can be configured to move toward one another when the plurality of blades move from the advanced configuration to the retracted configuration.

The plurality of blades can be configured in any number of ways. A distance between each of the plurality of blades in the retracted configuration can be less than a distance between each of the plurality of blades in the advanced configuration. At least one of the plurality of blades can be configured to move radially outward from a longitudinal axis of the elongate shaft when the plurality of blades are moved from the retracted configuration to the advanced configuration, and the at least one of the plurality of blades can be configured to move radially inward toward the longitudinal axis of the elongate shaft when the plurality of blades are moved from the advanced configuration to the retracted configuration. The plurality of blades can be biased to a position in which the plurality of blades are radially spaced apart from one another, e.g., the plurality of blades each being at least partially made from a shape memory material that allows the plurality of blades to automatically move away from one another. The curved distal ends of the plurality of blades can be oriented in a same direction as one another, and/or the curved distal ends can define a cutting path that matches the shape of a curved bone to be cut.

The surgical device can include at least one connection member connecting each of the plurality of blades together. The at least one connection member can be configured to move the plurality of blades apart when in the advanced configuration and to move the plurality of blades together when in the retracted configuration. A first end of the at least one connection member can be attached to a first one of the plurality of blades, and a second end of the at least one connection member can be attached to a second one of the plurality of blades adjacent to the first one of the plurality of blades.

A plurality of channels can extend at least partially through the inner passageway of the scraper tool. Each of the plurality of channels can have one of the plurality of blades disposed therein. The plurality of channels can include at least two channels, and at least two of the at least two channels can curve away from one another such that the channels are configured to direct the plurality of blades disposed therein away from one another when the plurality of blades are advanced distally therethrough.

The surgical device can include a locking mechanism coupled to the elongate shaft and configured to lock the plurality of blades in a fixed position along the longitudinal axis of the elongate shaft. In one embodiment, the locking mechanism can be a ratcheting mechanism.

In another embodiment, a surgical device is provided that includes an elongate shaft having an inner lumen extending through at least a distal portion thereof, and a blade assembly moveably disposed within at least a portion of the inner lumen. The blade assembly can have at least two blades with a first position in which the at least two blades are substantially coplanar with one another, and a second position in which cutting edges on each blade are spaced a distance apart from one another. The device can optionally include a biasing element configured to bias the cutting edges of the blades away from one another.

The blade assembly can vary in any number of ways. The blade assembly can have at least two blades, and more preferably at least three blades. Each of the at least two blades of the blade assembly can have a curved distal end. At least one of the at least two blades of the blade assembly can be disposed radially outward from a longitudinal axis of the elongate shaft.

In another aspect, a surgical method is provided that includes advancing a scraping device into a body of a patient such that the scraping device is positioned adjacent to a bone, extending a plurality of blades as a unit from the scraping device such that the plurality of blades move radially away from one another, and manipulating the scraping device to cause the plurality of blades to scrape a surface of the bone so as to create a desired geometry of the bone. The bone can be a femur, and a scraping surface of the bone can include removing a CAM lesion on the femur. After scraping the surface of the bone, the plurality of blades can be retracted as a unit into the scraping device. The scraping device can be removed from the body of the patient with the plurality of blades disposed within the scraping device.

BRIEF DESCRITION OF DRAWINGS

This invention will be more fully understood from the following detailed description taken in conjunction with the accompanying drawings, in which.

DETAILED DESCRIPTION

Figure 1:
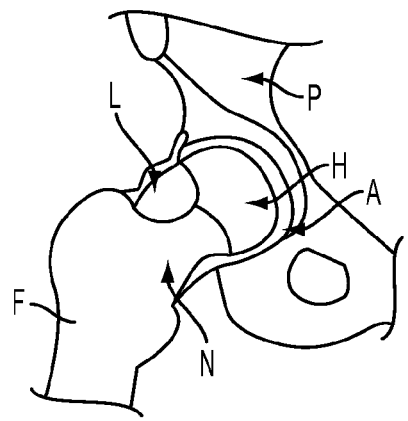
FIG. 1 (PRIOR ART) is a perspective view of a pelvis and a femur at a hip joint, the femur having a CAM lesion thereon.
Figure 2:
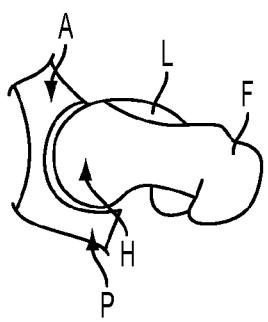
FIG. 2 (PRIOR ART) is a side, schematic view of the hip joint of FIG. 1.
Figure 3:
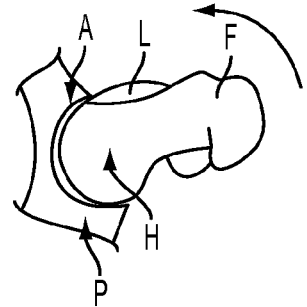
FIG. 3 (PRIOR ART) is a side, schematic view of the hip joint of FIG. 2 with the femur rotated upwards to a maximum extent permitted by the presence of the CAM lesion.
Figure 4:
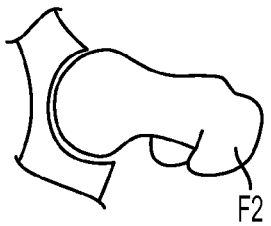
FIG. 4 (PRIOR ART) is a side, schematic view of a pelvis and a femur at a hip joint.
Figure 5:
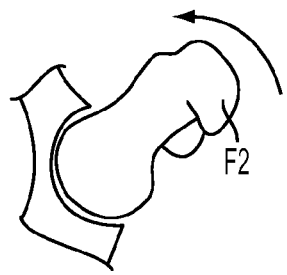
FIG. 5 (PRIOR ART) is a side, schematic view of the hip joint of FIG. 4 with the femur rotated upwards to a maximum extent possible.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for removing abnormalities from bone. In general, the methods and devices can allow excess bone to be scraped from a bone surface. In an exemplary embodiment, a scraper tool is provided that includes an elongate shaft having a plurality of blades movably disposed therein. The blades can be configured to move as a unit between a retracted configuration and an advanced configuration. In the retracted configuration, the blades can be entirely disposed within the elongate shaft, and in the advanced configuration, at least a distal portion of the blades can extend distally beyond the elongate shaft and/or be positioned a distance apart from one another. A distal portion of each of the blades can have a radius of curvature corresponding to a desired radius of curvature of the bone to be scraped, which can reduce a risk of accidental bone removal and/or damage to surrounding soft tissue and can mitigate need for constant visualization of the area being reshaped during surgery, e.g., by a camera, even where the surgeon may not have a complete understanding of the geometry of the bone abnormality to be removed. The scraper tool can be manipulated manually, e.g., by hand, thereby reducing the risk that the blades will deviate from a desired path of motion and cause accidental tissue removal and/or damage. The use of multiple blades to remove bone can increase a surface area of the bone being scraped at any given time and/or can help to orient the blades properly with respect to the bone, thus enhancing the efficiency of the surgery. Because the force of scraping is diffused across multiple blades, the chances of any one blade penetrating too deeply and/or puncturing the bone can be reduced.

Figure 6:
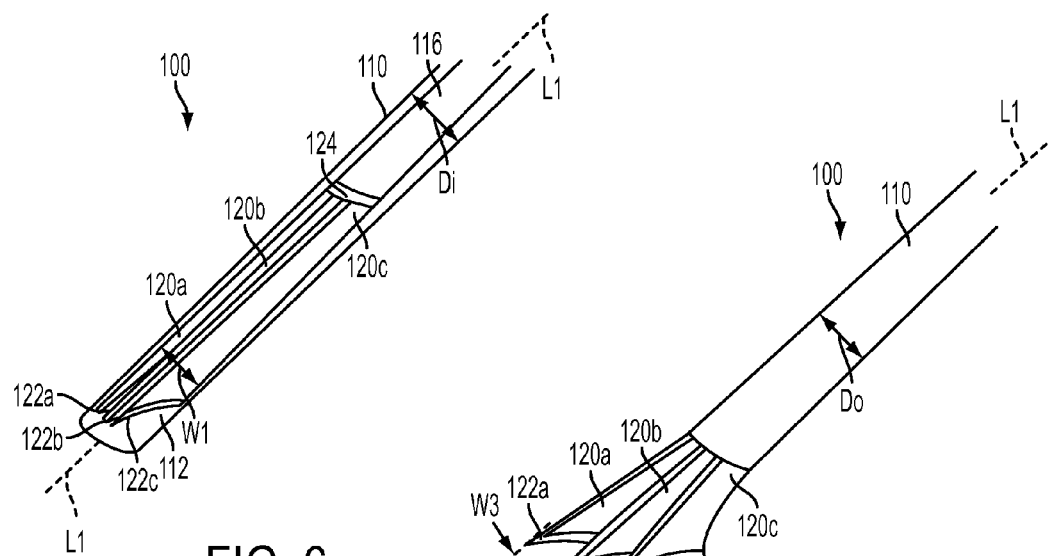
FIG. 6 is a perspective, partially transparent view of one embodiment of a scraper tool having a plurality of blades disposed therein shown in a retracted configuration.
Figure 7:
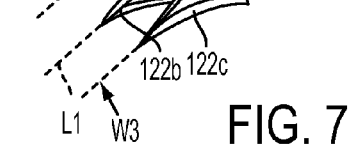
FIG. 7 is a perspective view of the scraper tool of FIG. 6 with the blades shown in an intermediate configuration between the retracted configuration and an advanced configuration.

FIGS. 6-9 illustrate one exemplary embodiment of a scraper tool 100 configured to scrape excess bone from a bone surface. The scraper tool 100 can include an elongate shaft 110 having a pusher shaft 116 and a plurality of blades 120a, 120b, 120c disposed therein. Although the scraper tool 100 in the illustrated embodiment includes three blades 120a, 120b, 120c, the scraper tool 100 can have any number of blades, e.g., one, two, three four, five, six, etc., same or different from one another, disposed therein. The blades 120a, 120b, 120c can be configured to move as a unit between a retracted configuration, shown in FIG. 6, and an advanced configuration, shown in FIG. 8. Between the retracted and advanced configurations, the blades 120a, 120b, 120c can be in an intermediate configuration, shown in FIG. 7. The intermediate configuration of FIG. 7 is an illustrative example of one of multiple intermediate configurations that the blades 120a, 120b, 120c can have as the blades 120a, 120b, 120c move between the retracted and advanced configurations, as discussed further below.

The elongate shaft 110 can have a variety of sizes, shapes, and configurations. Generally, the elongate shaft 110 can be configured to be inserted at least partially into a body of a patient. In an exemplary embodiment, at least a distal portion of the elongate shaft 110 can be constructed of a substantially rigid material to facilitate insertion into the patient and to help prevent the blades 120a, 120b, 120c from puncturing or otherwise damaging the elongate shaft 110, although a portion of the elongate shaft 110, e.g., a proximal portion, can be flexible. An inner passageway, or inner lumen 112, generally referred to herein as a "lumen," can extend along at least a distal portion of the elongate shaft 110 and can define a longitudinal axis L1. The lumen 112 can extend throughout an entire longitudinal length of the elongate shaft 110, such that the elongate shaft 110 has a cannulated interior, or it can extend through only a portion thereof including the distal end. The lumen 112 can have an inner diameter $D_i$ that is large enough in at least a distal portion thereof to accommodate the blades 120a, 120b, 120c therein, such that the blades 120a, 120b, 120c can move within the lumen 112 between the retracted configuration and the advanced configuration. The lumen 112 in the illustrated embodiment has a cylindrical shape and only one inner diameter $D_i$, but the lumen 112 can have any other shape and can varying inner diameters along a longitudinal length thereof. Similarly, the elongate shaft 110 in the illustrated embodiment has a cylindrical shape with an outer diameter $D_o$, but the elongate shaft 110 can have any other shape and a variety of outer diameters along the longitudinal length thereof.

The blades 120a, 120b, 120c can have a variety of sizes, shapes, and configurations. Generally, the blades 120a, 120b, 120c can be movable as a unit relative to the elongate shaft 110 to selectively allow first, second, and third cutting edges 122a, 122b, 122c of the first, second, and third blades 120a, 120b, 120c, respectively, to be exposed outside the elongate shaft 110 and hence be available for cutting, e.g., scraping, bone. The blades 120a, 120b, 120c in the retracted configuration can have a first width W1, shown in FIG. 6, that is less than the inner diameter $D_i$ of the lumen 112 in which the blades 120a, 120b, 120c are disposed. The blades 120a, 120b, 120c in the advanced configuration can have a second width W2, shown in FIG. 8, that is greater than the first width W1 and that can also be greater than the inner diameter $D_i$ of the inner lumen 112, as well as the outer diameter $D_o$ of the elongate shaft 110. The blades 120a, 120b, 120c can thus be configured to scrape a surface area of bone greater than a maximum outer diameter $D_o$ of the elongate shaft 110, shown in FIG. 8, and greater than a size of a portal through which the elongate shaft 110 having the blades 120a, 120b, 120c disposed therein is introduced into a body. The blades 120a, 120b, 120c can thus be effective for use in an arthroscopic surgical procedure and can be configured to scrape bone more quickly than a single blade or blade(s) having a width equal to or less than the outer diameter $D_o$ of the elongate shaft 110. As discussed further below, the blades 120a, 120b, 120c can be configured to automatically move between first and second widths W1, W2, which can ease use of the scraper tool 100.

The blades 120a, 120b, 120c can each have a longitudinal length, as measured from a distal-most end of the blades 120a, 120b, 120c to a proximal-most end of the blades 120a, 120b, 120c, that is smaller than the longitudinal length of the elongate shaft 110, such that the blades 120a, 120b, 120c can be disposed entirely within the elongate shaft 110 when the blades 120a, 120b, 120c are in the retracted configuration. The longitudinal length of the elongate shaft 110 can be, e.g., in a range of about 15 to 25 mm, and the longitudinal length of each of the blades 120a, 120b, 120c can correspondingly be, e.g., in a range of about 15 to 25 mm. Each of the blades 120a, 120b, 120c can have any width as measured along an axis perpendicular to a longitudinal axis of each of the blades 120a, 120b, 120c, e.g., in a range of about 3 to 5 mm, and each of the blades 120a, 120b, and 120c can have any thickness as measured along an axis perpendicular to the axis defining the width of each of the blades 120a, 120b, 120c, e.g., in a range of about 1 to 2 mm.

As mentioned above, the blades 120a, 120b, 120c can have cutting edges 122a, 122b, 122c on distal ends thereof. The cutting edges 122a, 122b, 122c can each have a radius of curvature corresponding to a radius of a bone surface, e.g., a surface of a femur head. The radii of the cutting edges 122a, 122b, 122c can, in an exemplary embodiment, be about 25 mm, but can be any value. In embodiments of scraper tools having more than one blade, the radius of the cutting edge of each blade can be either the same or different from the radii of the cutting edges of the other blade(s). The curvature of the cutting edges 122a, 122b, 122c can be concave as in the illustrated embodiment, although the curvature can be convex. A concave curvature, however, corresponds to a convex shape of typical bone abnormalities, such as CAM lesions, that protrude from a bone surface and are treated through removal. In the retracted configuration, the cutting edges 122a, 122b, 122c of each of the blades 120a, 120b, 120c can be oriented in substantially the same direction, such that the blades 120a, 120b, 120c can appear as a single blade when viewed from an axis perpendicular to the longitudinal axes of the blades 120a, 120b, 120c. In the advanced configuration, the cutting edges 122a, 122b, 122c can be oriented in substantially the same direction and can define a path that conforms to a curvature of a surface of a bone. The path can be a curved path, as indicated by opposite directional arrows A1, A2 in FIG. 8, which can facilitate scraping of a substantially curved or substantially hemi-spherical bone. The cutting edges 122a, 122b, 122c can define a spherical surface at least when the blades 120a, 120b, 120c are in the advanced configuration, although cutting edges can define a surface having another concave shape, such as cylindrical, ovular, saddle-shaped, etc. A femoral neck typically has a cylindrical shape or a saddle shape such that blades' cutting edges defining a cylindrical or saddle shape can be effective for reshaping a femoral neck. In another embodiment, the path can be a straight path, which can facilitate scraping of a substantially cylindrical bone.

In the retracted configuration, shown in FIG. 6, the blades 120a, 120b, 120c can be entirely disposed within the lumen 112, which can reduce a risk of tissue damage when the blades 120a, 120b, 120c are inserted into a patient. The blades 120a, 120b, 120c can be aligned within the lumen 112 such that the axis of each of the blades 120a, 120b, 120c is substantially parallel to the longitudinal axis L1 of the lumen 112 while in the retracted configuration. The blades 120a, 120b, 120c can be disposed side-by-side within the lumen 112. The longitudinal axis of at least one of the blades 120a, 120b, 120c can be coaxial with the longitudinal axis L1 of the lumen 112, and the longitudinal axes of the remaining blades 120a, 120b, 120c can be disposed radially outward from the longitudinal axis L1 of the lumen 112. In the illustrated embodiment, the longitudinal axis of the second blade 120b is coaxial with the longitudinal axis L1 of the lumen 112, and the longitudinal axes of the first and third blades 120a, 120c are disposed radially outward from the longitudinal axis L1 of the lumen 112. None of the longitudinal axes of the blades 120a, 120b, 120c need to be coaxial with the longitudinal axis L1 of the lumen 112.

In the intermediate configuration, shown in FIG. 7, at least a portion of each of the cutting edges 122a, 122b, 122c can extend beyond the distal end of the elongate shaft 110. The blades 120a, 120b, 120c can begin to flare radially away from the longitudinal axis L1 of the lumen 112, as discussed further below. The blades 120a, 120b, 120c can thus have a width W3 that is smaller than the width W2 of the blades 120a, 120b, 120c in the advanced configuration and that is larger than the width W1 of the blades 120a, 120b, 120c in the retracted configuration.

Figure 8:
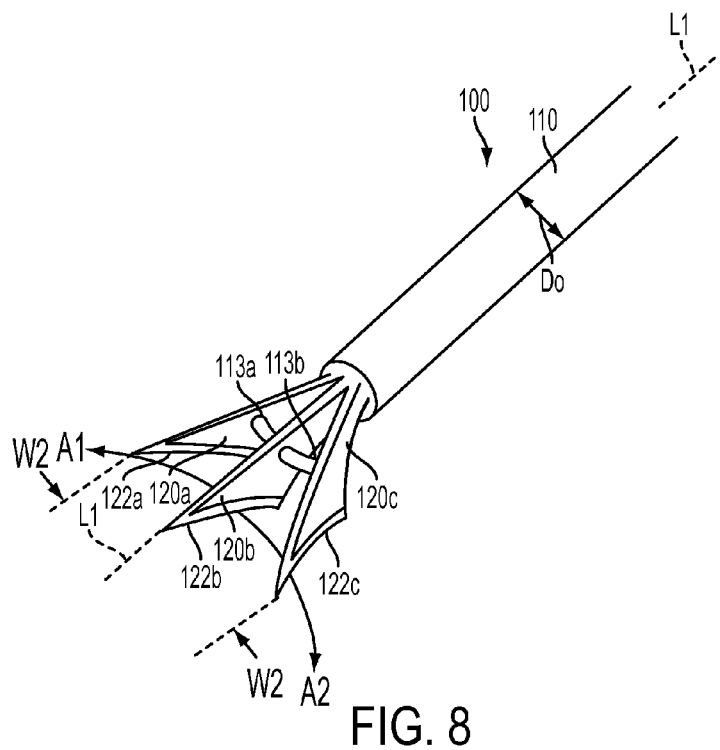
FIG. 8 is a perspective view of the scraper tool of FIG. 7 with the blades shown in the advanced configuration.
Figure 9:
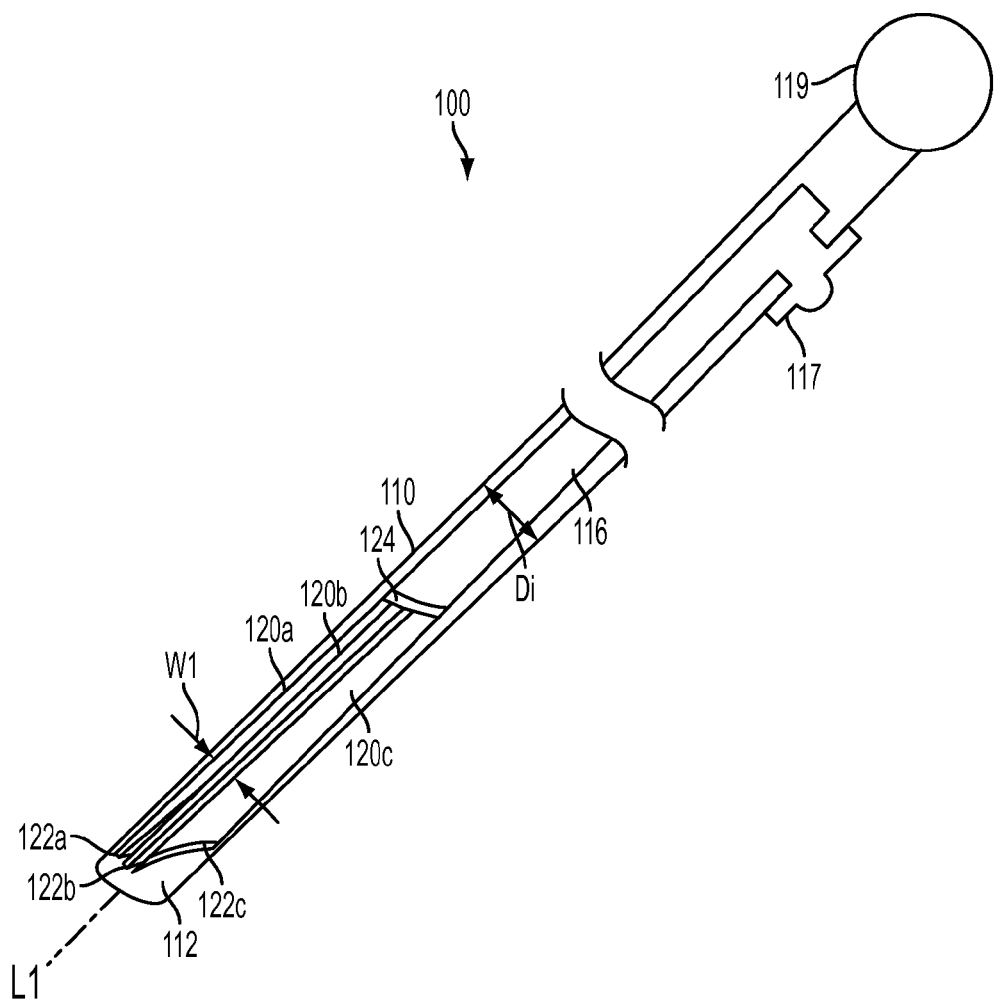
FIG. 9 is a perspective view of the scraper tool of FIG. 6 showing a proximal portion of the tool.

In the advanced configuration, shown in FIG. 8, the cutting edges 122a, 122b, 122c of the blades 120a, 120b, 120c can extend to a maximum extent distally beyond a distal end of the elongate shaft 110. In an exemplary embodiment, the cutting edges 122a, 122b, 122c can be positioned entirely outside the shaft 110 when the blades 120a, 120b, 120c are in the advanced configuration. The blades 120a, 120b, 120c can extend any distance beyond the distal end of the elongate shaft 110 when the blades 120a, 120b, 120c are in the advanced configuration. In an exemplary embodiment, the distance between the distal-most ends of the blades 120a, 120b, 120c and the distal end of the elongate shaft 110 can be about 10 to 15 mm.

In the advanced configuration, the blades 120a, 120b, 120c can flare away from one another, and hence also from the longitudinal axis L1 of the lumen 112. Thus, as discussed above, the blades 120a, 120b, 120c can have their larger width W2 in the advanced configuration, which can increase a surface area of the bone to be scraped and can impart stability to the user's movement of the scraper tool 100. In the advanced configuration, as with the retracted configuration, the longitudinal axis of at least one of the blades 120a, 120b, and 120c can be coaxial with the longitudinal axis L1 of the lumen 112. In the illustrated embodiment, the longitudinal axis of the second blade 120b is coaxial with the longitudinal axis L1 of the lumen 112 in both the retracted and the advanced configurations. In the advanced configuration, the longitudinal axes of the remaining blades 120a, 120b, 120c can flare radially outward from the longitudinal axis L1 of the lumen 112, such that the longitudinal axes along at least a distal portion of the remaining blades 120a, 120b, 120c are no longer substantially parallel to the longitudinal axis L1 of the lumen 112. In the illustrated embodiment, the distal portions of the longitudinal axes of the first and third blades 120a, 120c can flare radially outward from the longitudinal axis L1 of the lumen 112 when the blades 120a, 120b, 120c are in the advanced configuration. When the blades 120a, 120b, 120c are moved back to the retracted configuration, e.g., retracted proximally into the lumen 112, the longitudinal axes of the first and third blades 120a, 120c can move back to being substantially parallel to the longitudinal axis L1 of the lumen 112. In other words, in the illustrated embodiment, the distal portions of the first blade 12a and the third blade 120c can be configured to flare radially away from each other, the second blade 120b, and the longitudinal axis L1 of the lumen 112, while the second blade 120b can extend substantially parallel to the longitudinal axis L1 of the lumen 112 along the entire length of the blade 120b. In the advanced configuration of an embodiment having an odd number of blades, at least one, centrally disposed blade can extend substantially parallel to the longitudinal axis of the lumen, as with the second blade 120b, and the remaining blades, if any, as with the first and third blades 120a, 120c, can flare radially away from the longitudinal axis of the lumen along a distal portion of the blades. In the advanced configuration of an embodiment having an even number of blades, a distal portion of all of the blades can flare radially away from the longitudinal axis of the lumen.

The blades 120a, 120b, 120c can be configured to flare away from one another in a variety of ways. In the embodiment illustrated in FIG. 8, first and second connection members 113a, 113b can be configured to bias the first and third blades 120a, 120c away from the second blade 120b and from the longitudinal axis L1 of the lumen 112. The first connection member 113a can be connected at one end thereof to the distal portion of the first blade 120a and at an opposite end thereof to the distal portion of the second blade 120b, and the second connection member 113b can be connected at one end thereof to the distal portion of the second blade 120b and at an opposite end thereof to the distal portion of the third blade 120c. Although two connection members 113a, 113b are shown in the illustrated embodiment with one connection member extending between adjacent ones of the blades 120a, 120b, 120c, multiple connection members can extend between adjacent ones of the blades 120a, 120b, 120c. Similarly, a single connection member can extend across all of the blades 120a, 120b, 120c.

In the retracted configuration, the connection members 113a, 113b can be configured to be collapsed, and in the advanced configuration, the connection members 113a, 113b can be configured to be expanded. The connection members 113a, 113b are obscured in FIGS. 6 and 7. As in the illustrated embodiment, the connection members 113a, 113b can be in the form of bars that are slidably connected to one of the blades 120a, 120b, 120c at one end via slots (not shown) formed in the one of the blades 120a, 120b, 120c to which the connection member 113a, 113b is connected. In the retracted configuration, the connection members 113a, 113b can be positioned within the slots such that the connection members 113a, 113b are aligned substantially parallel to the blades 120a, 120b, 120c. In moving from the retracted configuration to the advanced configuration, the connection members 113a, 113b can be configured to slide within and out of the slots such that the connection members 113a, 113b are aligned substantially perpendicular to the blades 120a, 120b, 120c, as shown in FIG. 8. The connection members 113a, 113b can be biased to the perpendicular orientation shown in FIG. 8 by, e.g., a spring element, such that the connection members 113a, 113b automatically move between the parallel and perpendicular orientations as the blades 120a, 120b, 120c move between the retracted configuration and the advanced configuration. In another embodiment, the connection member(s) can be in the form of springs configured to expand when the blades to which the springs are attached move from the retracted configuration to the advanced configuration, and can be configured to compress when the blades move from the advanced configuration to the retracted configuration.

In another embodiment, the connection member(s) connecting the blades can be formed from a shape memory material such that the blades are biased to the advanced configuration. If the blades are formed from a shape memory material, as discussed further below, no connection members are necessary because the blades can be configured to selfexpand from the retracted configuration to the advanced configuration. However, connection member(s) can still be provided for stability. In some embodiments, the connection member(s) can be in the form of flexible metal bars that are configured to be bent in the retracted configuration and straightened when the blades to which the bars are connected move from the retracted configuration to the advanced configuration. Although the connection members 113a, 113b are identical in the illustrated embodiment, the connection members can be different from one another.

In some embodiments, one or more blades of a scraper tool can be formed from a shape memory material, which can include a single material or any combination of materials, such that at least distal portion(s) of the blade(s) are biased away from the other blade(s), if any, and/or from a longitudinal axis of an elongate shaft of the scraper tool when the blade(s) are in a resting configuration. In other words, one or more of the blade(s) can flare away from the longitudinal axis at a distal end thereof in the resting configuration. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The shape memory material can facilitate the blade(s) being biased to an expanded configuration in which the blade(s) are flared away from one another, as discussed above. The shape memory material can facilitate advancement of the blade(s) into tissue by allowing any or all portions of the blade(s) to be deformed or bent in a retracted configuration in which the blade(s) have a smaller width than a width thereof in an advanced configuration, while also allowing the blade(s) to automatically move from the retracted configuration to the advanced configuration. In an exemplary embodiment, the entirety of the blade(s) can be formed from one or more shape memory materials. In another exemplary embodiment, only the distal portion(s) of the blade(s) can be formed from one or more shape memory materials, and another portion of the blade(s), e.g., an intermediate portion from which the distal portion(s) extend, can be formed of a non-shape memory material, e.g., titanium, stainless steel, etc.

Referring again to the embodiment of FIGS. 6-9, the blades 120a, 120b, 120c can be configured to move between the retracted configuration and the advanced configuration in a variety of ways. The scraper tool 100 can include an actuator configured to be manually actuated by a user. The actuator can be disposed on a proximal portion of the scraper tool 100, which can facilitate handling of the actuator outside a patient's body. The illustrated embodiment also shows a handle 119 in the proximal portion of the device 100. By way of non-limiting example, the actuator can include a knob 117 operatively connected to the pusher shaft 116. The actuator, e.g., the knob 117, can be configured to be actuated via manual movement to move the blades 120a, 120b, 120c within the lumen 112 relative to the elongate shaft 110 using any power source, e.g., mechanical, electrical, magnetic, etc. As in the illustrated embodiment, the actuator can be configured to function to selectively advance and retract the pusher shaft 116 that is slidably disposed within the lumen 112 by sliding the knob 117 distally and proximally, respectively. The knob 117 can be configured to be manually held in place to maintain the blades 120a, 120b, 120c in a selected position relative to the shaft 110. The knob 117 can include two detents that signify a locked position in which the knob 117 and the blades 120a, 120b, 120c are held in a fixed position relative to the shaft 110 and an unlocked position in which the knob 117 and the blades 120a, 120b, 120c can be movable relative to the shaft 110. The actuator can be configured to move between the locked and unlocked positions in a variety of other ways. In another embodiment, a knob or other actuator can include a ratchet that biases the actuator and the blades to the locked position. The knob or other actuator can be configured to be pressed down, e.g., pressed radially inward toward the shaft's longitudinal axis, to move from the locked position to the unlocked position. When the knob or other actuator stops being pressed down, the knob or other actuator can be configured to automatically move radially outward, e.g., away from the shaft's longitudinal axis, to move from the unlocked position to the locked position. As will be appreciated by a person skilled in the art, the knob or other actuator can be configured to be locked and unlocked in other ways, such as by a push and release button, a movable and lockable switch, etc. Other embodiments of actuators include a handle, a lever, a button, a switch, etc.

The pusher shaft 116 can be operatively coupled to the actuator and to the blades 120a, 120b, 120c, either fixedly or removably, in a variety of ways, e.g., corresponding engagement members, adhesive, etc. In the illustrated embodiment, a distal end of the pusher shaft 116 includes a hub 124 configured to fixedly mate the blades 120a, 120b, 120c to the pusher shaft 116. In an embodiment where blades are removably coupled to a pusher shaft, the blades can be removed between surgical procedures and replaced with identical blades or blades having, e.g., different sizes, shapes, materials, etc. In another embodiment, the blades can form a blade assembly that can be removably attached to the pusher shaft 116, thus allowing for attachment and removal of the blade assembly as a unit between surgical procedures. Actuation of the actuator, e.g., moving a handle, pushing a button, moving a lever, flipping a switch, etc., can be configured to move the pusher shaft 116, and hence also the blades 120a, 120b, 120c, relative to the elongate shaft 110.

The scraper tool 100 can include a locking mechanism configured to lock the blades 120a, 120b, 120c in the retracted configuration, in the advanced configuration, or in any intermediate configuration between the retracted and advanced configurations. In one embodiment, the blades 120a, 120b, 120c can be biased to the retracted configuration by, e.g., a spring, such that the locking mechanism can be configured to lock the blades 120a, 120b, 120c in an intermediate or in the advanced configuration. When the locking mechanism is in an unlocked position, the blades 120a, 120b, 120c can be configured to automatically retract into the lumen 112, which can reduce the risk of accidental bone removal and/or soft tissue damage when the scraper tool 100 is disposed within a body. The locking mechanism can be coupled to the proximal portion of the scraper tool 100 and can include an actuator, e.g., a button, a knob, a switch, etc., configured to be manually manipulated by a user. The locking mechanism can be configured to hold the blades 120a, 120b, 120c in place, e.g., such as with a ratcheting mechanism. The locking mechanism can be configured to reduce a risk of accidental retraction of the blades 120a, 120b, 120c to the retracted configuration when the blades 120a, 120b, 120c are in an advanced configuration or in the intermediate configuration during scraping of the bone. The locking mechanism, by allowing locking of the blades 120a, 120b, 120c in the intermediate configuration, can allow for a user to select a desired blade length extending beyond the distal end of the elongate shaft 110, thereby allowing the scraper tool 100 to be effective in small surgical spaces and/or in crowded surgical spaces.

The scraper tool 100 can include a proximal handle configured to facilitate manual handling of the tool 100. The handle can have a variety of sizes, shapes, and configurations, as will be appreciated by a person skilled in the art.

The scraper tool 100 can be configured to be manually manipulated in use, which can help reduce a risk of accidental bone removal and/or soft tissue damage. In another embodiment, a scraper tool can include a vibrating feature that causes blades movably disposed in an elongate shaft of the scraper tool to vibrate, which can facilitate bone removal. The vibrating feature can be configured in a variety of ways, as will be appreciated by a person skilled in the art. The vibrating feature can be coupled to an actuator, e.g., a switch, a button, or a knob, such that the vibration can be selectively turned on and off by a user. Similarly, the blades can include an ultrasound feature that can be selectively utilized to facilitate bone removal.

Figure 10:
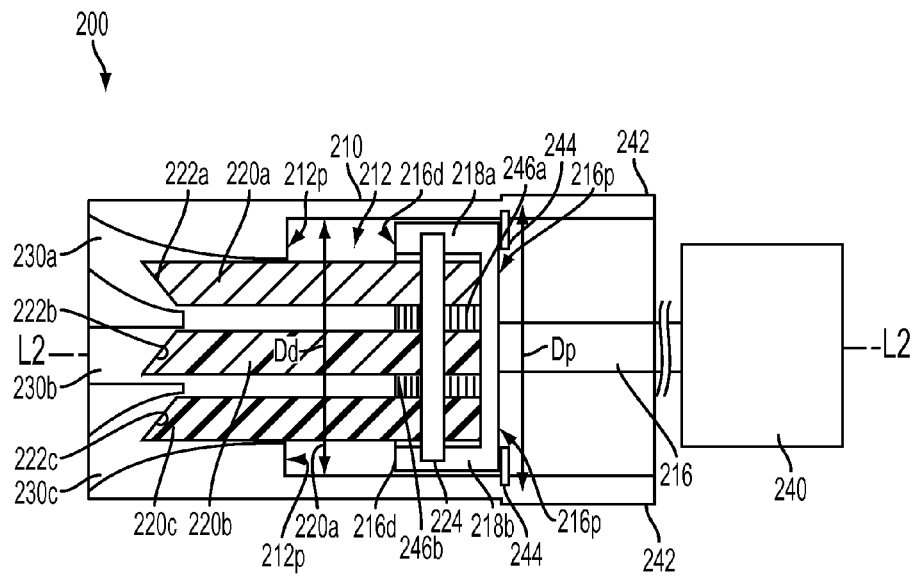
FIG. 10 is a side, partially transparent view of another embodiment of a scraper tool having a plurality of blades disposed therein shown in a retracted configuration.
Figures 11, 12, 13:
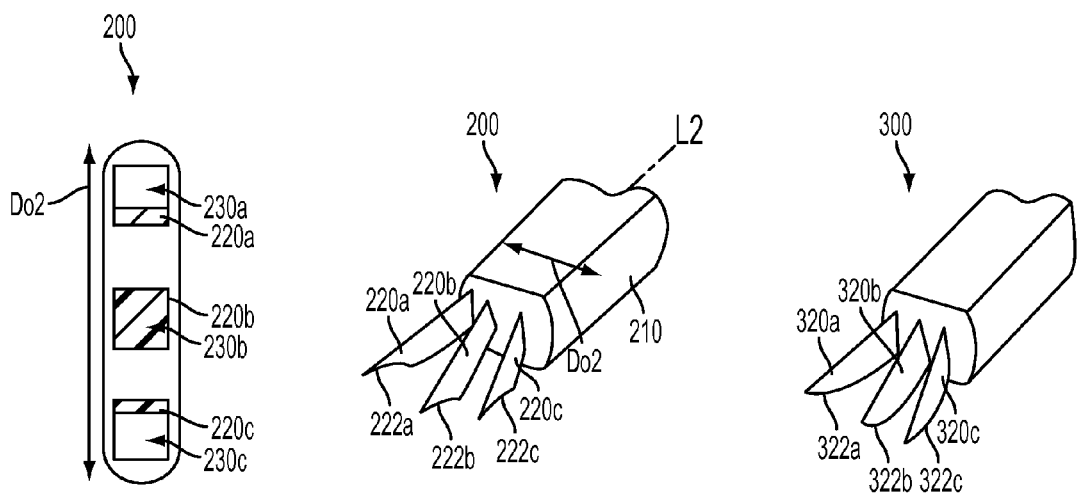
FIG. 11 is a distal end view of the scraper tool of FIG. 10.
FIG. 12 is a perspective view of the scraper tool of FIG. 10 with the blades positioned in an advanced configuration.
FIG. 13 is a perspective view of another embodiment of a scraper tool having blades with concave cutting edges and positioned in an advanced configuration.

Another embodiment of a scraper tool 200 is illustrated in FIGS. 10-12. The scraper tool 200, as well as other scraper tools described herein, can generally be configured and used similar to the scraper tool 100 of FIGS. 6-9. Additionally, like-named elements and like-illustrated elements of the scraper tool 100 and of the other scraper tools discussed herein can be configured and used similar to one another.

The scraper tool 200 can include an elongate shaft 210 having a lumen 212 extending therethrough. A distal portion of the lumen 212 can be divided into a plurality of channels 230a, 230b, 230c. The lumen 212 in the illustrated embodiment includes first, second, and third channels 230a, 230b, 230c, which correspond to a number of blades 220a, 220b, 220c disposed within the scraper tool 200. The channels 230a, 230b, 230c can each be configured to slidably seat one of the first, second, and third blades 220a, 220b, 220c, such that the blades 220a, 220b, 220c can be guided through the channels 230a, 230b, 230c as the blades 22a, 220b, 220c move as a unit between a retracted configuration and an advanced configuration, similar to that discussed above. The channels 230a, 230b, 230c can be configured to guide at least a distal portion of at least one of the blades 220a, 220b, 220c radially outward from a longitudinal axis L2 of the lumen 212 as the blades 220a, 220b, 220c are advanced distally out of the elongate shaft 210. In the illustrated embodiment, curved portions along distal ends of the first and third channels 230a, 230c can be configured to guide the first and third blades 220a, 220c radially outward from the longitudinal axis L2 of the lumen 212 as the first and third blades 220a, 220c move out of the elongate shaft 210. The second channel 230b can be uncurved and can extend coaxially with the longitudinal axis L2 of the lumen 212 along an entire longitudinal length of the second channel 230b, thus guiding the second blade 220b in a straight path as the second blade 220b moves out of the elongate shaft 210. At least the first and third blades 220a, 220c can be formed from material(s) and have a thickness configured to allow curved movement through curved distal portions of the first and third channels 230a, 230c. Once the first and third blades 220a, 220c exit their respective curved channels 230a, 230c, the first and third blades 220a, 220c can be configured to straighten out. Cutting edges 222a, 222b, 222c of the blades 220a, 220b, 220c can thus be properly aligned relative to one another for scraping bone despite some of the blades 220a, 220b, 220c exiting the elongate shaft 210 along curved trajectories.

To ensure that the blades 220a, 220b, 220c move within the paths of the channels 230a, 230b, 230c, at least a portion of the blades 220a, 220b, 220c can be disposed within the channels 230a, 230b, 230c when the blades 220a, 220b, 220c are in the retracted configuration, as shown in FIG. 10, and in the advanced configuration. Thus, each of the blades 220a, 220b, 200c can have a longitudinal length that is greater than a distance that the blades 220a, 220b, 220c extend beyond the distal end of the elongate shaft 210 in the advanced configuration. In other words, the blades 220a, 220b, 220c can each have a longitudinal length such that a proximal portion of each of the blades 220a, 220b, 220c is disposed within the lumen 212 when the blades 220a, 220b, 220c are in the advanced configuration.

The curvature of the channels can vary depending on a number of blades in a scraper tool and/or on a bone which the tool is configured to scrape. In an embodiment having an odd number of channels, at least one, centrally disposed channel can extend coaxially with a longitudinal axis of an elongate shaft along the centrally disposed channel's entire longitudinal length, as in the illustrated embodiment of FIGS. 10-12, and the remaining channels, if any, can flare radially outward from the longitudinal axis of the elongate shaft along at least a distal portion thereof. In an embodiment having an even number of channels, all of the channels can flare radially outward from a longitudinal axis of an elongate shaft along at least a distal portion thereof.

Referring again to FIGS. 10-12, the blades 220a, 220b, 220c can be configured to move as a unit from the retracted configuration, shown in FIGS. 10 and 11, to the advanced configuration, shown in FIG. 12, by manipulation of a handle 240 in a proximal portion of the scraper tool 200. The handle 240 can have a variety of sizes, shapes, and configurations. The handle 240 can be configured to move the blades 220a, 220b, 220c relative to the elongate shaft 210, e.g., as an actuator for the blades 220a, 220b, 220c. In the illustrated embodiment, the handle 240 can be operatively connected at a distal end thereof to a pusher shaft 216, which can be operatively connected at a distal end thereof to the blades 220a, 220b, 220c. Thus, advancing the handle 240 distally with respect to the elongate shaft 210 can advance the blades 220a, 220b, 220c distally from the retracted configuration to the advanced configuration, with the intermediate configuration therebetween. Correspondingly, moving the handle 240 proximally with respect to the elongate shaft 210 can retract the blades 220a, 220b, 220c from the advanced configuration to the intermediate configuration, and from the intermediate configuration to the retracted configuration. During movement of the handle 240, an outer handle 242 at the proximal portion of the elongate shaft 210 can be held such that the handle 240 moves relative to the elongate shaft 210.

The scraper tool 200 can include a proximal stop mechanism configured to stop proximal movement of the handle 240, and hence the blades 220a, 220b, 220c at a certain point, which can help keep at least a portion of the blades 220a, 220b, 220c within the channels 230a, 230b, 230c when the blades 220a, 220b, 220c are in the retracted configuration. The proximal stop mechanism can have a variety of sizes, shapes, and configurations. In the illustrated embodiment, the proximal stop mechanism includes a retaining ring 244 extending circumferentially around the lumen 212 and having a diameter $D_p$ that is smaller than an outer diameter $D_{o2}$ of the elongate shaft 210. A proximal surface 216p of the pusher shaft 216 can be configured to abut the retaining ring 244 when the blades 220a, 220b, 220c are in the retracted configuration. The proximal stop mechanism can thus define a proximal-most position of the blades 220a, 220b, 220c.

The scraper tool 200 can also include a distal stop mechanism. The distal stop mechanism can have a variety of sizes, shapes, and configurations, such as a retaining ring. In the illustrated embodiment, the distal stop mechanism includes a distal surface 216d having a diameter $D_d$ that is smaller than the outer diameter $D_{o2}$ of the elongate shaft 210. The distal surface 216d can be configured to abut a proximal surface 212p of the elongate shaft 210 within the lumen 212 when the blades 220a, 220b, 220c are in the advanced configuration. The distal stop mechanism can thus define a distal-most position of the blades 220a, 220b, 220c.

The pusher shaft 216 can be coupled to the blades 220a, 220b, 220c in a variety of ways. As in the illustrated embodiment, a proximal portion of the blades 220a, 220b, 220c can be received in a cavity defined between opposed arms 218a, 218b of the pusher shaft 216. At least one rivet 224 can be connected at opposite ends to the opposed arms 218a, 218b and can be coupled to the blades 220a, 220b, 220c so as to couple the blades 220a, 220b, 220c to the pusher shaft 216. A second rivet (not shown), opposite to the rivet 224, can similarly be coupled to the pusher shaft 216 and/or to the blades 220a, 220b, 220c. The blades 220a, 220b, 220c can be connected to either one or both of the pusher shaft 216 and the rivet 224, and either one or both of the pusher shaft 216 and the rivet 224 can be configured to advance and retract the blades 220a, 220b, 220c as a unit relative to the elongate shaft 210. In one embodiment, the blades 220a, 220b, 220c can be removably coupled to the pusher shaft 216 and/or the rivet 224, e.g., using interference fit, snap-fit, light adhesive, etc. The blades 220a, 220b, 220c can be removed by, e.g., advancing the blades 220a, 220b, 220c to the advanced configuration and applying a distal force to the blades 220a, 220b, 220c. First and second washers 246a, 246b can be disposed between adjacent ones of the blades 220a, 220b, 220c adjacent to the rivet 224. The washers 246a, 246b, e.g., rubber washers, can be configured to help keep the blades 220a, 220b, 220c appropriately spaced so as to be movably disposed within the channels 230a, 230b, 230c.

The blades 220a, 220b, 220c of the scraper tool 200 can be configured similarly to the blades 120a, 120b, 120c of the scraper tool 100 as described above. The blades 220a, 220b, 220c can each have cutting edges 222a, 222b, 222c with radii of curvature, either same or different, that correspond to a radius of curvature of a bone to be scraped. The cutting edges 222a, 222b, 222c can have a concave curvature, as shown in FIG. 12. Alternatively, as shown in an embodiment illustrated in FIG. 13, blades 320a, 320b, 320c of a scraper tool 300 can have cutting edges 322a, 322b, 322c, each having a convex curvature, corresponding to a concave curvature of a bone to be scraped.

The scraper tools disclosed herein can be generally used to scrape abnormalities from a bone. In an exemplary embodiment, a scraper tool can be used to remove a CAM lesion formed on a head of a femur.

In use, a scraper tool can be inserted into a body of a patient such that the scraper tool is positioned adjacent to a bone. The scraper tool can be inserted into the body in any number of ways, as will be appreciated by a person skilled in the art, such as through a slotted cannula. During insertion, a plurality of blades disposed within the scraper tool can be in a retracted configuration, in which the blades are entirely disposed within an elongate shaft of the scraper tool. Once the elongate shaft is advanced to the desired position near a bone, the blades can be distally advanced beyond a distal end of the elongate shaft by, e.g., actuation of an actuator, to an advanced configuration, as described above, or to an intermediate configuration between the retracted and advanced configurations. The blades can optionally be locked in the advanced configuration or in an intermediate configuration by actuating a locking mechanism of the scraper tool. With the blades in the intermediate configuration or, in an exemplary embodiment, in the advanced configuration, the scraper tool can be moved over the surface of the bone such that the blades scrape a bone abnormality to create a desired geometry of the surface of the bone. The blades can be manually moved in a back and forth motion. Movement of the blades can optionally be visualized, e.g., using a camera, which can help ensure that the blades do not scrape or otherwise damage unintended matter within the body. The bone abnormality can be scraped so as to be entirely removed. Bone debris resulting from the scraping can be suctioned out of the body by, e.g., a vacuum or suction through a cannulation of the scraper tool. After the bone abnormality has been removed entirely or to a desired extent, the blades can be retracted back to the retracted configuration by actuating the actuator, and the scraper tool can be removed from the patient. The scraper tool can be removed from the patient with the blades in the intermediate configuration or the advanced configuration, but having the blades retracted within the elongate shaft during removal can help prevent the blades from cutting or otherwise damaging tissue and/or other material.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
advancing a scraping device into a body of a patient such that the scraping device is positioned adjacent to a bone having an abnormality thereon;
extending a plurality of blades as a unit from the scraping device such that the plurality of blades move radially apart from one another, a distal portion of each of the blades having a radius of curvature corresponding to a desired geometry of a surface of the bone; and
manipulating the scraping device to cause the plurality of blades to scrape the abnormality at least partially off the bone so as to create the desired geometry of the surface of the bone.

2. The method of claim 1, wherein the bone comprises a femur, and scraping the surface of the bone comprises removing a CAM lesion on the femur.

3. The method of claim 1, further comprising, after scraping the surface of the bone, retracting the plurality of blades as a unit into the scraping device, and removing the scraping device from the body of the patient with the plurality of blades disposed within the scraping device.

4. A surgical method, comprising:
advancing an elongate shaft into a body of a patient;
distally advancing a plurality of blades as a unit to move a cutting edge of each of the plurality of blades beyond a distal end of the elongate shaft, the distal advancement of the plurality of blades automatically causing a lateral distance between adjacent ones of the blades to increase;
positioning the cutting edges adjacent an abnormality on a bone of the patient, the cutting edges each having a radius of curvature; and
manipulating the plurality of blades to cause the cutting edges to scrape away at least a portion of the abnormality from the bone and thereby reshape a surface of the bone to have a radius of curvature corresponding to a radius of curvature defined by the radii of curvature of the cutting edges.

5. The method of claim 4, wherein the radii of curvature of the cutting edges are the same as one another.

6. The method of claim 4, wherein the radii of curvature of the cutting edges are not the same as one another.

7. The method of claim 4, wherein the bone comprises a femur, and scraping away at least a portion of the abnormality from the bone comprises removing a CAM lesion on the femur.

8. The method of claim 4, further comprising, after scraping away at least a portion of the abnormality from the bone, retracting the plurality of blades as a unit into the elongate shaft, and removing the elongate shaft from the body of the patient with the plurality of blades disposed within the elongate shaft.

* * * * *